US009243902B2

United States Patent
Atac et al.

(10) Patent No.: US 9,243,902 B2
(45) Date of Patent: Jan. 26, 2016

(54) SYSTEM FOR LIGHT SOURCE LOCATION DETECTION

(71) Applicant: THALES VISIONIX, INC., Clarksburg, MD (US)

(72) Inventors: Robert B. Atac, Batavia, IL (US); Eric Foxlin, Lexington, MA (US)

(73) Assignee: Thales Visionix, Inc., Clarksburg, MD (US)

( * ) Notice: Subject to any disclaimer, the term of this patent is extended or adjusted under 35 U.S.C. 154(b) by 0 days.

(21) Appl. No.: 14/209,636

(22) Filed: Mar. 13, 2014

(65) Prior Publication Data

US 2015/0226546 A1   Aug. 13, 2015

Related U.S. Application Data

(63) Continuation-in-part of application No. 13/559,332, filed on Jul. 26, 2012.

(60) Provisional application No. 61/511,811, filed on Jul. 26, 2011, provisional application No. 61/798,733, filed on Mar. 15, 2013.

(51) Int. Cl.

| G01N 21/00 | (2006.01) |
|---|---|
| G01B 11/26 | (2006.01) |
| G01N 21/68 | (2006.01) |
| G01N 21/64 | (2006.01) |
| G01S 3/784 | (2006.01) |
| G01J 3/02 | (2006.01) |

(52) U.S. Cl.
CPC ............... *G01B 11/26* (2013.01); *G01N 21/64* (2013.01); *G01N 21/68* (2013.01); *G01S 3/784* (2013.01); *G01J 3/02* (2013.01)

(58) Field of Classification Search
CPC ... H01J 37/32935; G01N 21/64; G01N 21/68; G01N 2015/1037; G01J 3/02
USPC ...................................... 356/300–445, 72–73
See application file for complete search history.

(56) References Cited

U.S. PATENT DOCUMENTS

| 3,678,283 | A |   | 7/1972 | Labaw |  |
|---|---|---|---|---|---|
| 4,568,188 | A | * | 2/1986 | Weber et al. | ............... 356/636 |
| H192 | H |   | 1/1987 | Daehler |  |
| 5,196,689 | A |   | 3/1993 | Sugita et al. |  |
| 5,510,893 | A |   | 4/1996 | Suzuki |  |
| 5,748,321 | A | * | 5/1998 | Burks et al. | ............... 356/635 |
| 5,926,264 | A |   | 7/1999 | Beale et al. |  |
| 6,424,410 | B1 |   | 7/2002 | Pelosi |  |
| 8,619,267 | B2 | * | 12/2013 | Wong et al. | ............... 356/623 |

(Continued)

OTHER PUBLICATIONS

"Laser Spot Tracker, Model 742DP", Analog Modules, Inc., Sep. 2010.

(Continued)

*Primary Examiner* — Abdullahi Nur
(74) *Attorney, Agent, or Firm* — Arent Fox LLP

(57) ABSTRACT

Aspects of the present invention relate to systems, methods, and computer program products for tracking an orientation of a first object. The system includes a light emitting device located relative to a second object at a fixed predetermined position; a sensor having a photodetector array that is configured to receive incident light emitted from the light emitting device, the photodetector array being mounted on the first object; and a processor coupled to the photodetector array, the processor configured to determine the orientation of the first object relative to the second object based on an angle of incident light detected by the photodetector array from the light emitting device.

20 Claims, 10 Drawing Sheets

(56) References Cited

U.S. PATENT DOCUMENTS

| | | |
|---|---|---|
| 2004/0149036 A1 | 8/2004 | Foxlin et al. |
| 2010/0109976 A1 | 5/2010 | Gilbert et al. |
| 2011/0273722 A1 | 11/2011 | Charny et al. |
| 2012/0001071 A1 | 1/2012 | Snider et al. |

OTHER PUBLICATIONS

"Pacific Silicon Sensor Series 6 Data Sheet, Quad Sum and Difference Amplifier", Part Description QP50-6-18u-SD2 Order # 10-027, Sep. 24, 2010, pp. 1-2.

"Two-Dimensional PSD S5990-01, S5991-01, Improved Tetra-Lateral Type for Surface Mounting", Hamamatsu Photonics K.K., Solid State Division, Dec. 2007.

Dohyung Kim et al., "Optical Tracker for Augmented Reality and Wearable Computer", Interdisciplinary Computational Systems Laboratory, 1997, pp. 1-7.

Kiran K. Gunnam et al., "A Vision-Based DSP Embedded Navigation Sensor", IEEE Sensors Journal, Oct. 2002, vol. 2, No. 5, pp. 428-442.

International Search Report and Written Opinion mailed Apr. 1, 2015 for corresponding International Application No. PCT/US2014/028068.

* cited by examiner

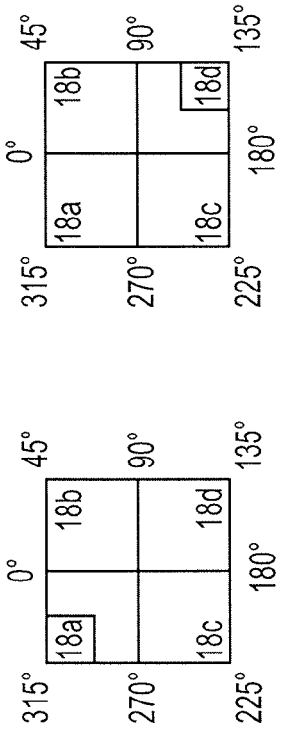
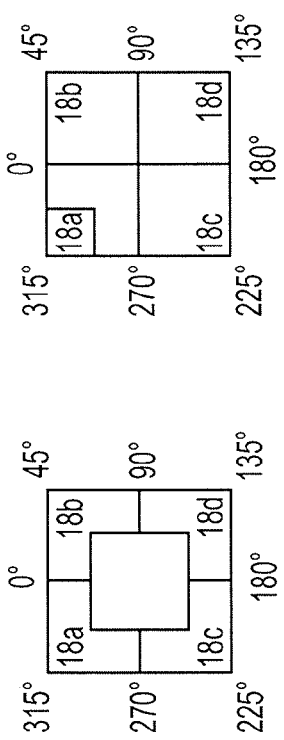
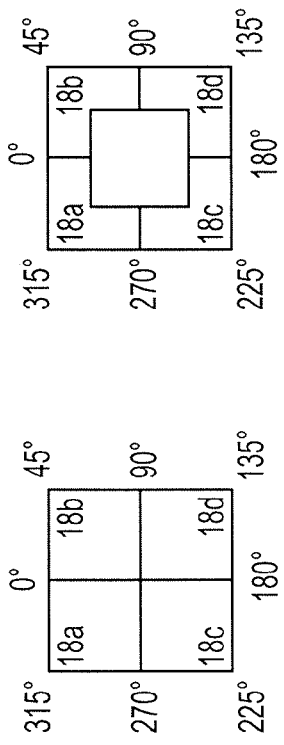
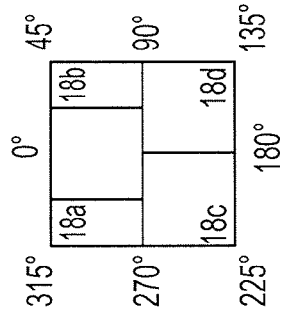
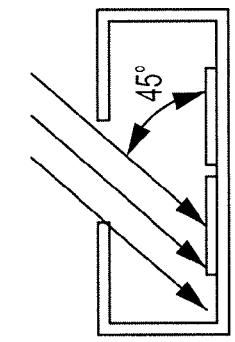
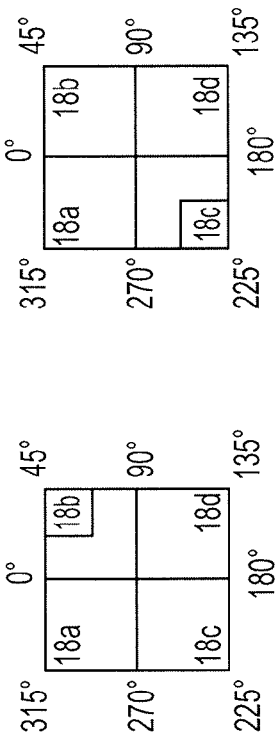

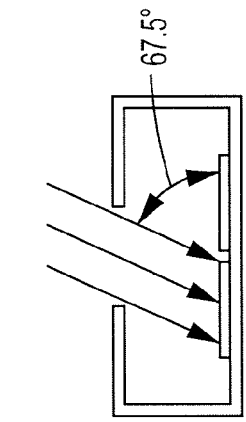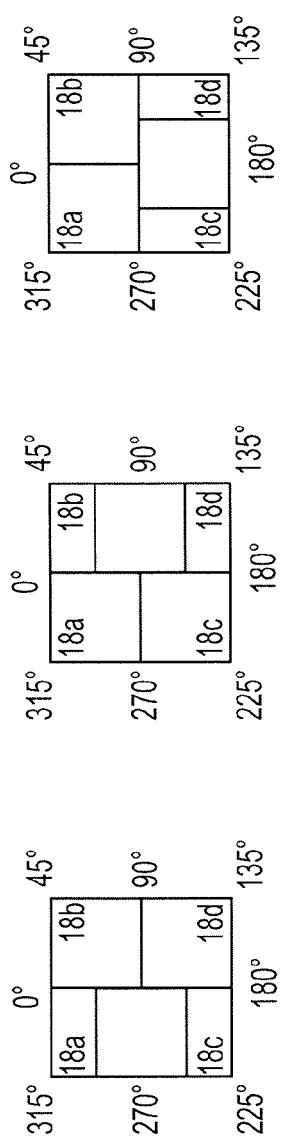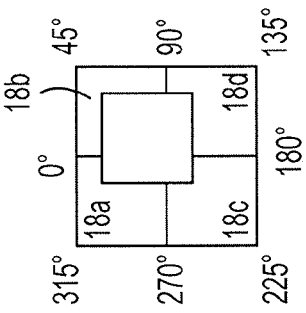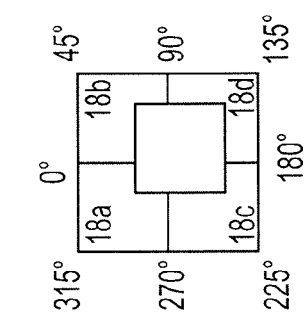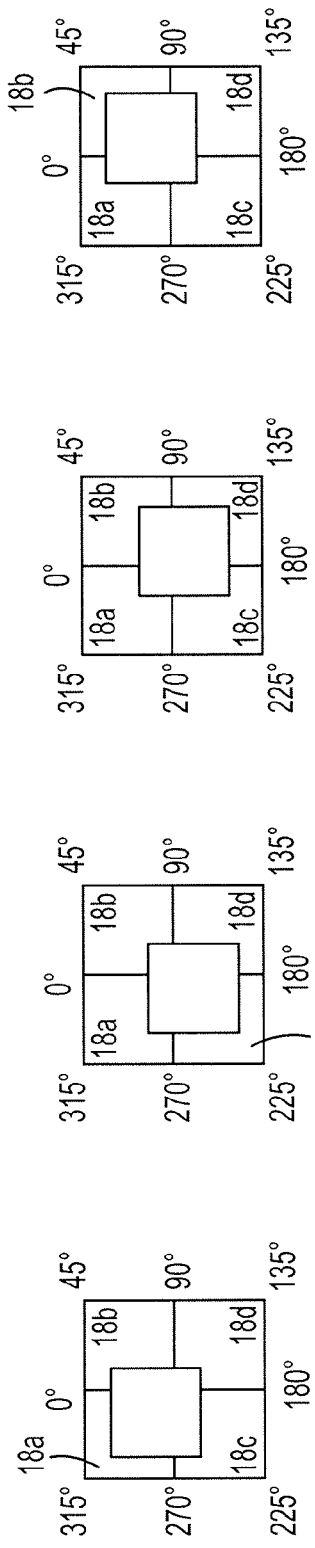

SYSTEM FOR LIGHT SOURCE LOCATION DETECTION

CLAIM OF PRIORITY

The present Application for Patent is a Continuation-in-Part of Non-Provisional patent application Ser. No. 13/559,332 entitled "Sensing Direction and Distance" filed Jul. 26, 2012, which claims priority to Provisional Application No. 61/511,811 filed Jul. 26, 2011, and the present Application for Patent also claims priority to Provisional Application No. 61/798,733 entitled "System for Light Source Location Detection" filed Mar. 15, 2013; and, each of the above-noted applications is assigned to the assignee hereof and hereby expressly incorporated in its entirety by reference herein.

BACKGROUND

Aspects of the present invention generally relate to light source location detection and, more particularly, to systems for gunfire detection and for helmet orientation detection.

SUMMARY

According to an aspect of the present invention, a system for detecting a light source may include a housing having a front side and a back side, the back side being opposed to the front side and spaced therefrom; a photodetector array with at least two pixels located at the back side wall within the housing; an aperture extending through the front side of the housing that is spaced from the photodetector array an equivalent distance as the size of the aperture and configured to expose the photodetector array to an incident light from the light source; and a processor coupled to the plurality of photocells and configured to detect the light source.

According to another aspect of the present invention, a system for tracking an orientation of a first object may include a light emitting device located relative to a second object at a fixed predetermined position; a sensor having a photodetector array that receives incident light emitted from the light emitting device, the photodetector array being mounted on the first object; and a processor coupled to the photodetector array, the processor being configured to determine the orientation of the first object relative to the second object based on an angle of incident light detected by the photodetector array from the light emitting device.

According to yet another aspect of the present invention, a system for detecting a direction from an object to a first light source may include an optical sensor mounted with a predetermined orientation on the object, the optical sensor configured to detect the first light source and to measure the direction to the first light source with respect to the optical sensor; and a processor configured to transform the direction of the first light source with respect to the optical sensor into a direction with respect to the object using the predetermined orientation of the optical sensor on the object.

According to yet another aspect of the present invention, a method for tracking an orientation of a first object may include emitting a light via a light emitting device located relative to a second object at a fixed predetermined position; detecting, via a sensor having a photodetector array, the light emitted from the light emitting device, the photodetector array being mounted on the first object; and determining, via a processor coupled to the photodetector array, the orientation of the first object relative to the second object based on an angle of the light detected by the photodetector array from the light emitting device.

According to yet another aspect of the present invention, a method for detecting a direction from an object to a first light source may include detecting, via an optical sensor mounted with a predetermined orientation on the object, the first light source; measuring, via the optical sensor, the direction to the first light source with respect to the optical sensor; and transforming, via a processor, the direction of the first light source with respect to the optical sensor into a direction with respect to the object using the predetermined orientation of the optical sensor on the object.

According to yet another aspect of the present invention, a system for tracking an orientation of a first object may include means for emitting a light, wherein the emitting means is located relative to a second object at a fixed predetermined position; means for detecting the light emitted from the means for emitting, the means for detecting being mounted on the first object; and means for determining the orientation of the first object relative to the second object based on an angle of the light detected by the detecting means.

According to yet another aspect of the present invention, a system for detecting a direction from an object to a first light source may include means for detecting the first light, the means for detecting being mounted with a predetermined orientation on the object; means for measuring the direction to the first light source with respect to the means for detecting; and means for transforming the direction of the first light source with respect to the means for detecting into a direction with respect to the object using the predetermined orientation of the means for detecting on the object.

According to yet another aspect of the present invention, a computer program product may include a non-transitory computer-readable medium having control logic stored therein for causing a computer to track an orientation of a first object, the control logic including code for emitting a light via a light emitting device located relative to a second object at a fixed predetermined position; code for detecting, via a sensor having a photodetector array, the light emitted from the light emitting device, the photodetector array being mounted on the first object; and code for determining, via a processor coupled to the photodetector array, the orientation of the first object relative to the second object based on an angle of the light detected by the photodetector array from the light emitting device.

According to yet another aspect of the present invention, a computer program product may include a non-transitory computer-readable medium having control logic stored therein for causing a computer to detect a direction from an object to a first light source, the control logic including code for detecting, via an optical sensor mounted with a predetermined orientation on the object, the first light source; code for measuring, via the optical sensor, the direction to the first light source with respect to the optical sensor; and code for transforming, via a processor, the direction of the first light source with respect to the optical sensor into a direction with respect to the object using the predetermined orientation of the optical sensor on the object.

It is understood that other aspects of the invention will become readily apparent to those skilled in the art from the following detailed description, wherein various aspects of the present invention are shown and described by way of illustration only. As will be understood, the present invention is capable of other and different variations and its several details are capable of modification in various other respects, all without departing from the scope of the invention. Accordingly, the drawings and detailed description are to be regarded as illustrative in nature and not as restrictive.

BRIEF DESCRIPTION OF THE DRAWINGS

These and other sample aspects of the disclosure will be described in the detailed description and the appended claims that follow, and in the accompanying drawings, wherein:

FIGS. 8A-8P show a plurality of top views of states of a photodetector array of the sensor of FIG. 1 exposed to light at various incident angles in accordance with an exemplary aspect of the present invention;

Figure 1:
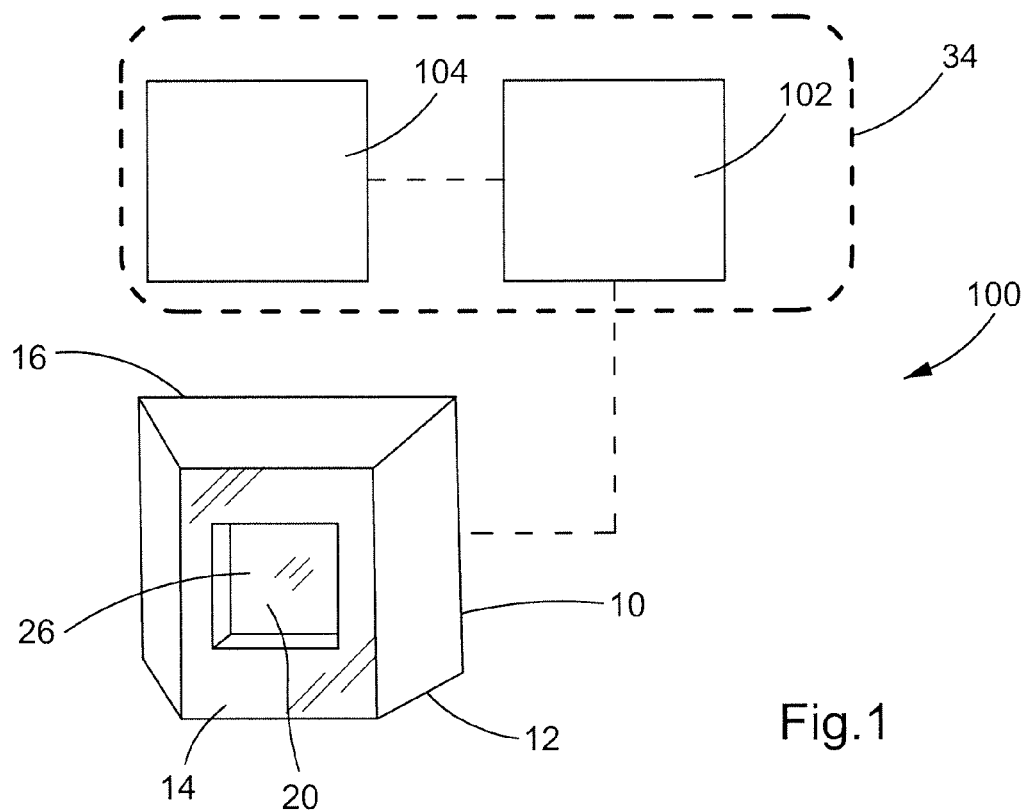
FIG. 1 is a schematic view of a system for light source location in accordance with an exemplary aspect of the present invention.

In accordance with common practice, the various features illustrated in the drawings may be simplified for clarity. Thus, the drawings may not depict all of the components of a given apparatus or method. In addition, like reference numerals may be used to denote like features throughout the specification and figures.

DETAILED DESCRIPTION

Various aspects of the present invention are described below. It should be apparent that the teachings herein may be embodied in a wide variety of forms and that any specific structure, function, or both being disclosed herein may be merely representative. Based on the teachings herein one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using other structure, functionality, or structure and functionality, in addition to or other than one or more of the aspects set forth herein. An aspect may comprise one or more elements of a claim.

Referring to the drawings in detail, wherein like reference numerals indicate like elements throughout, there is shown in FIGS. 1-9 a system, generally designated with reference numeral 100, for detecting the location of a light source, in accordance with exemplary aspects of the present invention.

A gunfire detection system that can identify the spatial location and/or the elevation angle of gunfire can be useful in warfare situations, for example, to identify azimuthal and/or elevation angle of a gun user such as a sniper. As such, it is desirable to have a gunfire detection system that is simple in design, physically robust, and functions reliably under a variety of conditions, including under chaotic war conditions and/or inclement weather conditions.

In order to maximize utility of a gunfire detection system on a battle field, for example, while minimizing the likelihood of it malfunctioning, it is desirable for the gunfire detection system to operate effectively without reliance on any complicated hardware and software packages. Therefore, a need exists for a gunfire detection system that is simple in design, economical, and preferably physically small in size. Such a simple gunfire detection system is more likely to function reliably under various environmental conditions, including inclement weather and battlefield conditions, than a gunfire detection system requiring expensive (magnifying/miniaturizing) lens systems, a camera, and/or complicated computer-implemented image processing components and algorithms.

Furthermore, a gunfire detection system that comprises simple components that are readily available and/or do not require extensive customization is easier to maintain and to replace if it malfunctions. Thus, the gunfire detection system can be designed not only to be wearable and/or mountable on a person's appendage or a headgear, such as a helmet, but also to be readily repairable and/or replaceable if it malfunctions.

Another advantage of having a gunfire detection system that is physically dimensioned to be easily wearable and/or mountable on a person's appendage, clothing or a headgear, such as a helmet, is that a plurality of the sensors can be distributed to and be worn by many individuals, who can independently of one another, detect gunfire. Also, a plurality of gunfire detection sensors can be mounted onto a headgear or clothing or appendage of a single individual, each sensor being configured to monitor a specific range of azimuth angles so that the plurality of the gunfire detection sensors can collectively monitor the entire range of azimuth angles: from 0° (north) through 90° (east), 180° (south), 270° (west), and up to 360° (north again). and elevation angles above the horizon from: 0° (at the horizon) up to 90° (at the zenith), down to 0° (at the horizon in the opposite direction) and below the horizon (downward) from 0° (at the horizon) to −90° (at the nadir), and from the nadir up to 0° (at the horizon again).

A system for detecting light source location, such as gunfire, in accordance with the present invention, in some aspects, includes a sensor which comprises a housing; a photodetector array configured to sense light that enters the housing through an aperture in a side of the housing. In one aspect, the aperture is configured to expose the photodetector array to light from a light source; and a processor coupled to the photodetector array and configured to detect the position, direction and/or location of the light source.

Figure 2:
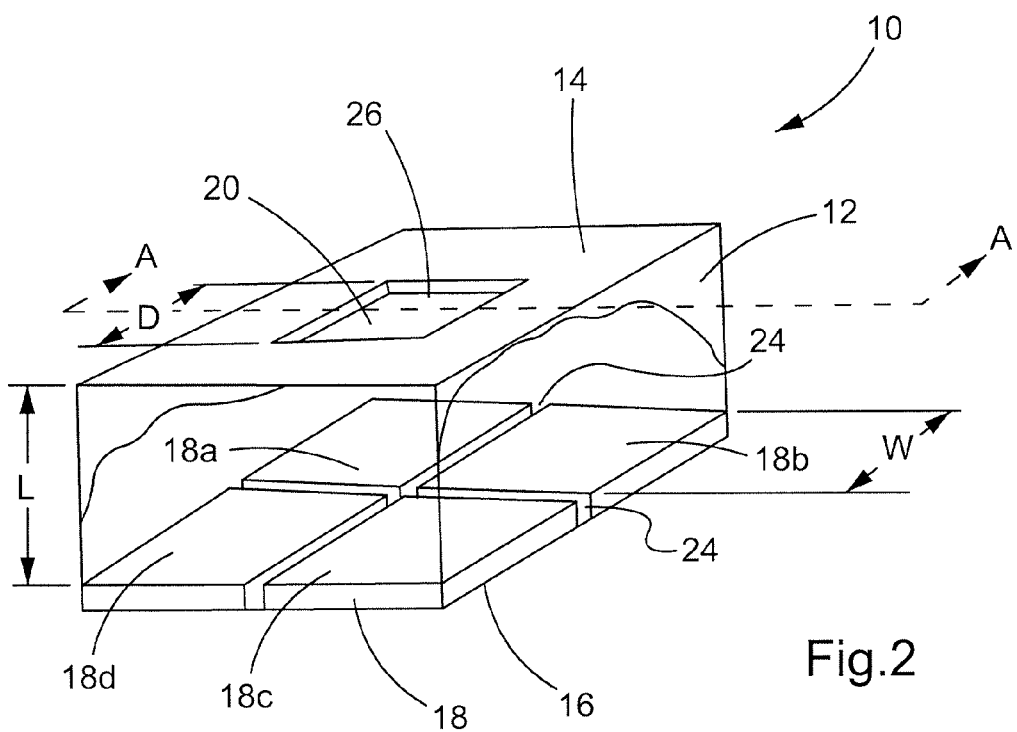
FIG. 2 is a perspective cutaway view of a sensor in the system of FIG. 1 in accordance with an exemplary aspect of the present invention.

Referring to FIGS. 1 and 2, a system 100 for detecting light location in accordance with an exemplary aspect of the present invention includes a sensor 10; sensor 10 having a housing 12; housing 12 having a front side 14 and a back side 16, wherein back side 16 is opposed to front side 14 and spaced therefrom. Housing 12 serves as a protective cover to protect components of sensor 10 from certain physical impacts, inclement weather or any other adverse environmental conditions. In one aspect, housing 12 is opaque.

In one aspect, sensor 10 includes a photodetector array 18 located within housing 12 at the backside 16 of housing 12. In one aspect, photodetector array 18 comprises two or more photodetectors 18a-18d. In one aspect, each photodetector 18a-18d comprises one pixel. In one aspect, each photodetector 18a-18d comprises a plurality of pixels. In some aspects, each photodetector 18a-18d comprises a plurality of photocells and/or photoresistors. In one aspect, photodetector array 18 comprises at least two pixels. In another aspect, photodetector array 18 is configured to receive light that enters housing 12 of sensor 10 through aperture 20 in front side 14 of housing 12. In one aspect, photodetector array 18 outputs a signal indicating a detection of light from an incident light impinging on one or more photodetectors 18a-18d. In one aspect of photodetector array 18, photodetectors 18a-18b, shown in FIGS. 2-6, are spaced apart from each other by gap 24.

Figure 4:
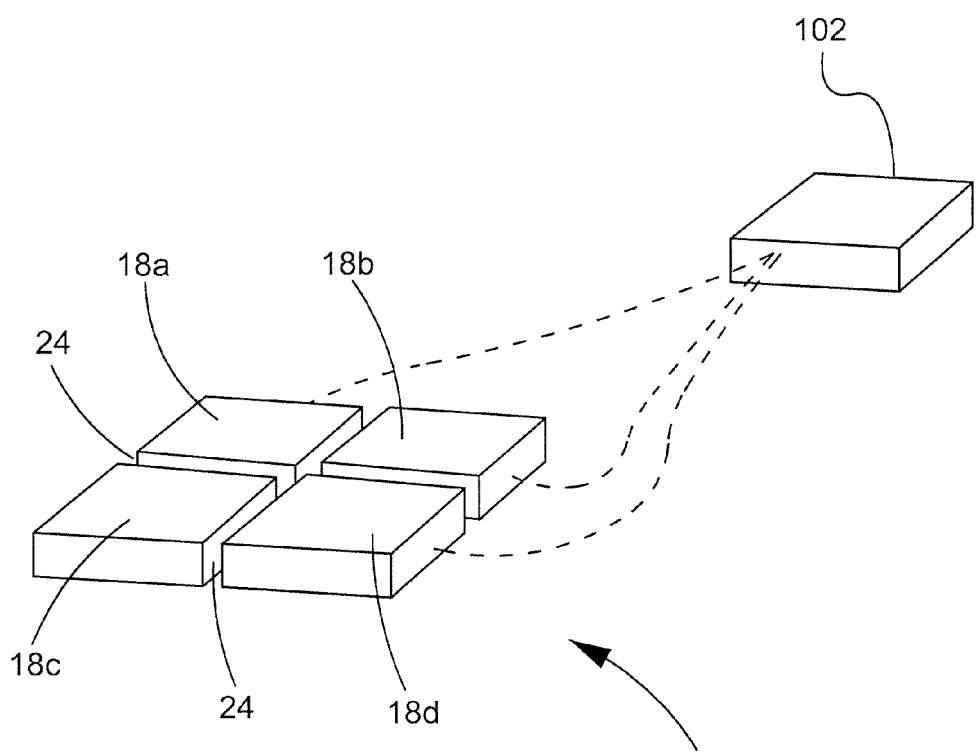
FIG. 4 is a perspective view of the photodetector array of the sensor shown in FIG. 2 coupled to a processor in accordance with an exemplary aspect of the present invention.

In one aspect, as shown in FIGS. 2 and 4, sensor 10 includes photodetector array 18 comprising a two-by-two array of photodetectors 18a-18d. In another aspect, as shown in FIG. 4, processor 102 is coupled to photodetector array 18. In one aspect, photodetector array 18 may be of any suitable shape, including square shape and rectangular shape. In another aspect, photodetector array 18 may have any suitable physical dimensions. In another aspect, photodetector array 18 is configured to produce an electrical signal in response to the presence or absence of incident electromagnetic radiation. In another aspect, photodetector array 18 is configured to sense an incident electromagnetic radiation in or adjacent to the ultraviolet, visible or infrared frequency ranges. In an aspect, photodetector array 18 is configured to produce a spectrum of responses depending on the frequency of the incident electromagnetic radiation. In another aspect, photodetector array 18 is configured to be more sensitive to radiation within a certain frequency range (e.g., 400 THz to 790 THz or a wavelength of from wavelengths from about 900 nm to about 1100 nm) without producing a corresponding electrical signal when radiated with light of an adjacent or a remote frequency range.

In one aspect, front side 14 of housing 12 has a window or an aperture 20 extending through it and configured to receive light from the environment of sensor 10 and expose at least a portion of the interior of housing 12 to the received light. As shown in FIG. 2, backside 16 defines a wall at which photodetector array 18 may be located within housing 12. In another aspect, processor 102 analyzes output signals of photodetector array 18 and calculates spatial parameters in order to detect a light source, such as gunfire. In one aspect, processor 102 may be further coupled to a head-mounted display (HMD), a computer, and/or a database 104. Processor 102, in some aspects, is coupled to head-mounted display (HMD), computer, and/or database 104 via one or more wires. In other aspects, processor 102 is wirelessly coupled to head-mounted display (HMD), computer, and/or database 104.

Figure 3:
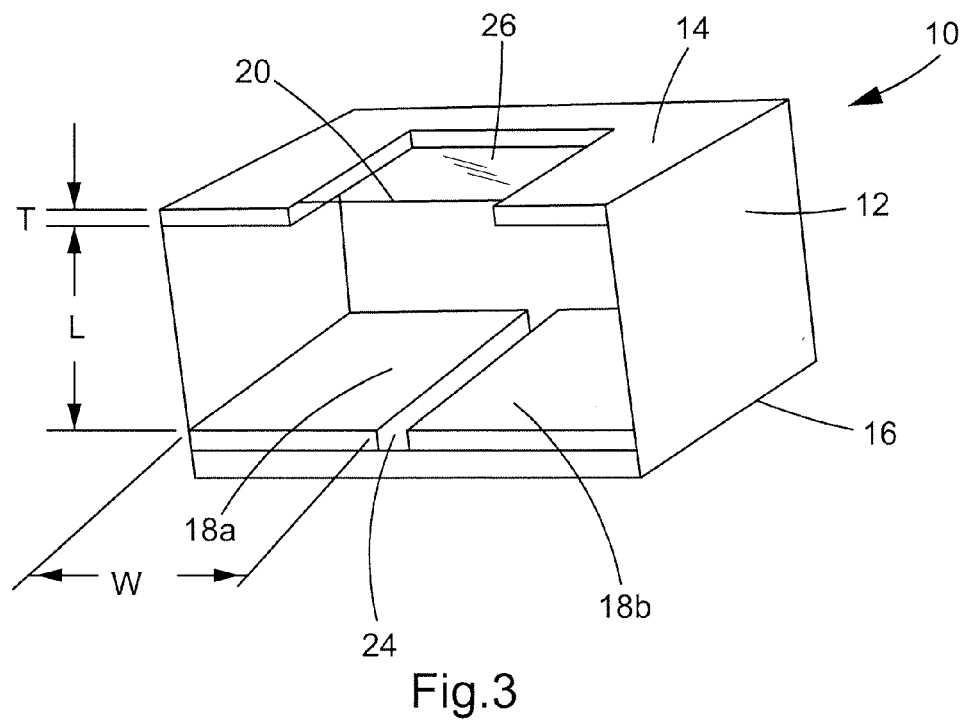
FIG. 3 is sectional view of the sensor of FIG. 2 taken along the line A-A in accordance with an exemplary aspect of the present invention.

Referring to FIGS. 1 and 2, in one aspect, housing 12 of sensor 10 is configured to allow exposure of at least a portion of the interior of housing 12 only to light entering housing 12 through aperture 20, which extends through front side 14 of housing 12. In one aspect, as shown in FIG. 3, housing 12 has a thickness T. In another aspect, housing 12 has a thickness T configured to be sufficiently small relative to length or width D of aperture 20 to allow photodetector array 18 to be exposed to greater amount of light entering housing 12 through aperture 20. In one aspect, length or width D of aperture 20 has a value that is substantially equal to the height or width W of a square or rectangular at least one of photodetectors 18a-18d. In one aspect, aperture 20 is configured to expose photodetector array 18 located at the backside wall of backside 16 within housing 12 to an incident light, resulting from a source such as gunfire. Although aperture 20, as shown in FIGS. 1 and 2, is square in shape, aperture 20 of any suitable shape and/or size may be used. In one aspect, aperture 20 has a length or width D. In another aspect, aperture 20 is rectangular, slit, circular or other preferred shapes.

Figure 5:
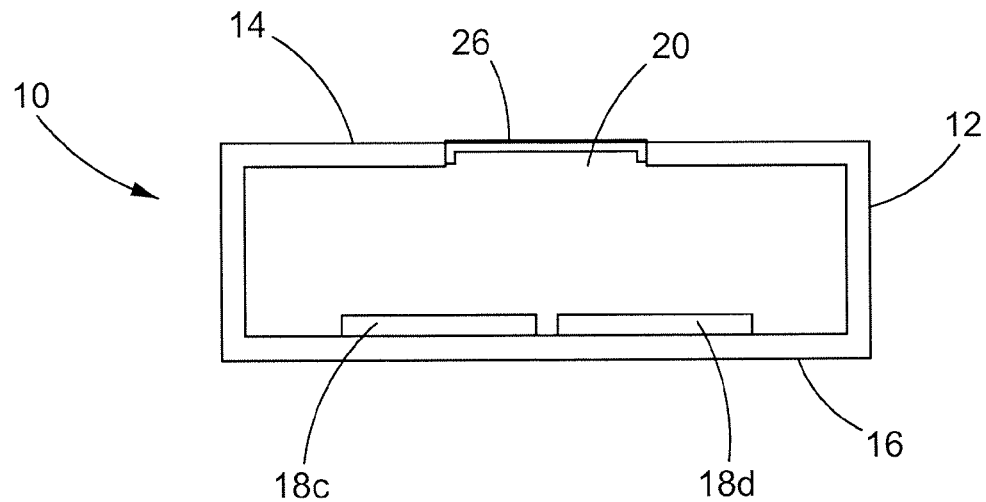
FIG. 5 is a schematic cross-sectional side view of the sensor of FIG. 1 in accordance with an exemplary aspect of the present invention.

In one aspect, as shown in the aspects of FIGS. 2 and 3, the center of aperture 20 is symmetrically aligned with the center of photodetector array 18 located within housing 12. In some aspects, an advantage of the symmetrical arrangement of aperture 20 is that it simplifies any computations that may be performed to reveal spatial orientation (e.g., azimuth, direction) and/or elevation angle of light source. In one aspect, such as shown in FIG. 5, sensor 10 includes an aperture cover 26 covering aperture 20. In another aspect, aperture cover 26 is flush with aperture 20. In another aspect, aperture cover 26 is positioned within housing 12. In another aspect, aperture cover 26 is disposed in aperture 20. In another aspect, aperture cover 26 extends across front side 14 and aperture 20. In one aspect, aperture 20 is a transparent portion of housing 12.

In one aspect, aperture cover 26 is configured to permit light coming from a light source to pass through aperture 20 without substantially distorting (e.g., bending, magnifying or miniaturizing) the light. In another aspect, aperture cover 26 is configured to permit light to pass through aperture 20 with minimal distortion (magnification or miniaturization) of the light. In another aspect, aperture cover 26 provides further protection for the components of sensor 10 against adverse environmental conditions, including inclement weather and dust particles.

In one aspect, aperture cover 26 is comprised of a transparent material. In one aspect, aperture cover 26 is comprised of plastic, glass, quartz or any other transparent material or a combination thereof. However, any suitable material that can permit passage of light therethrough with minimal distortion (magnification or miniaturization) of light can be used. In some aspects, sensor 10 has no lens within aperture 20 or housing 12. In one aspect, aperture cover 26 decreases the expense and weight of sensor 10. In other aspects, cover 26 includes a lens to magnify or miniaturize the incident light entering aperture 20. In one aspect, cover 26 is used to magnify or miniaturize the incident light entering aperture 20 in order to alter the range of light source detection.

Referring to FIGS. 2 and 4, in one aspect, sensor 10 includes photodetector array 18. In one aspect, sensor 10 includes includes a photodetector array 18 having a two-by-two array of photodetectors 18a-18d. In another aspect, at least one of photodetectors 18a-18b is arranged to be illuminated/activated by an incident light entering sensor 10 through aperture 20. In one aspect, each photodetector 18a-18d includes at least one photocell and/or photoresistor that is configured to be illuminated/activated by a portion of incident light and to generate an output signal/reading, which may be compared with the output signals of other activated photocells and/or photoresistors within photodetector array 18 to provide information about spatial orientation (an azimuth and/or an elevation) of the source of the incident light, e.g. gunfire.

In one aspect, aperture 20 is a distance L from photodetector array 18. In one aspect, distance L is equal to lateral width or length W of a photodetector 18a, 18b, 18c, or 18d.

In one aspect, each photodetector 18a-18d detects whether it has been exposed to light or no light. In one aspect, each photodetector 18a-18d comprises a binary photocell or a photoresistor. In one aspect, an advantage of having each photodetector 18a-18d comprising a binary photocell or photoresistor is that the symmetry of photodetector array 18 simplifies any computations required to compare output signals (light intensity readings) of the constituent binary photocells and/or photoresistors. As, shown FIGS. 6 and 8, different entrance (incident) angles of light, each represented by three parallel lines in FIG. 6, entering sensor 10 through aperture 20, lead to activation of different regions of the light-receiving surface of the photodetector array 18. Accordingly, while the shown photodetector array 18 comprises only four photodetectors 18a-18d in a two-by-two array arrangement, there are at least fourteen (14) potentially distinguishable states of photodetector array 18, as shown in FIGS. 8A-8N, depending on whether a set of 0, 1, 2, 3 or 4 of photodetectors 18a-18d is activated by an incident light. For example, in a two-by-two array of photodetectors 18a-18d, when none of photodetectors 18a-18d is exposed to light, the state of photodetector array 18 is illustrated by FIG. 8A. When all four of photodetectors 18a-18d are exposed to light, as shown in FIG. 8B, the incident light is striking all of photodetectors 18a-18d at an incident elevation angle of approximately normal to the plane of photocells, or along the sensor central optical axis, and/or photodetector array 18, indicating the light source is directly above sensor 10. In another example, if only one of photodetectors 18a-18d is exposed to light, as shown in FIGS. 8C-8F, incident light is striking the surface of the photodetector array 18 at an incident elevation angle of approximately 45° relative to the plane of photodetector array 18 and is originating from a light source located approximately in the same direction as photodetectors 18a-18d located diagonally relative to one of photodetectors 18a-18d that is exposed to the light. In other words, the light source is at an elevation angle of approximately 45° relative to the plane of photodetector array 18 as shown in FIG. 8G and is located at an azimuth of 135° relative to the top edge center of sensor 10 of FIG. 8C, an azimuth of 315° relative to the top edge center of sensor 10 of FIG. 8D, at an azimuth of 225° relative to the top edge center of sensor 10 of FIG. 8E, or at an azimuth of 45° relative to the top edge center of the sensor 10 of FIG. 8F.

In another example, if two adjacent photocells and/or photoresistors 18a-18d are exposed to light, as shown in FIGS. 8H-8K, the elevation angle of incidence is approximately 67.5° relative to the plane of the photodetector array 18 as shown in FIG. 8L and the light source is in the same direction as the opposite photodetectors 18a-18d. In other words, the light source is at an incident elevation angle of approximately 67.5° relative to the plane of photodetector array 18 and is located at an azimuth of 180° relative to the plane of sensor 10 in the case of FIG. 8H, at an azimuth of 90° relative to the plane of sensor 10 in the case of FIG. 8I, at an azimuth of 270° relative to the plane of sensor 10 in the case of FIG. 8J, or at an azimuth of 0° relative to the plane of sensor 10 in the case of FIG. 8K. In another example, if three adjacent photocells 18 are exposed to light, as shown in FIGS. 8M-8P, the light is striking photodetector array 18 at an incident elevation angle that is greater than 67.5° but less than 90° relative to the plane of photodetector array 18 and the light source is located in the same direction as the other photodetectors 18a-18d that are not exposed to light. In other words, the light source is at an incident elevation angle between 45° and 90° relative to the plane of photodetector array 18 and is located at an azimuth of 135° relative to the plane of sensor 10 in the case of FIG. 8M, at an azimuth of 45° relative to the plane of sensor 10 in the case of FIG. 8N, at an azimuth of 315° relative to the plane of sensor 10 in the case of FIG. 8O, or at an azimuth of 225° relative to the plane of sensor 10 in the case of FIG. 8P.

In some aspects of the present invention, the photodetectors in FIGS. 8A-8P may be analog photodetectors, and may be used when all four cells are receiving some light, so that ratios can be computed to determine precise angles to the light source. For example, in an aspect of the present invention, the sensor is primarily used as an analog direction sensor. This mode of operation corresponds to the situation when all four quadrants receive at least a some of the light spot, as illustrated in FIGS. 8B, 8M, 8N, 8O, and 8P. In one aspect, examples of photodetectors suitable for use in accordance with the present invention are described in U.S. patent application Ser. No. 13/559,332, filed Jul. 26, 2012, titled "Sensing Direction and Distance," which is incorporated herein by reference in its entirety.

Additional states of photodetector array 18 may be specified based on a percentage of the different regions of photodetector array 18 that is activated by an incident light. Accordingly, there are potentially more than 14 states of the aspect of photodetector array 18 having a two-by-two array of photodetectors 18a-18d that may be specified and used to specify spatial location/direction/orientation of light source with high level of granularity. Although sensor 10 is being illustrated herein as having photodetector array 18 comprising a two-by-two array of photodetectors 18a-18d, sensor 10 may have photodetector array 18 that comprises any number of photodetectors 18a-18d.

Accordingly, in one aspect, sensor 10 may include photodetector array 18 includes a plurality of photodetectors 18a-18d arranged in at least two rows. In another aspect, each row of photodetectors 18a-18d may be arranged in a single plane. In a further aspect, each row of photodetectors 18a-18d includes at least two photodetectors. In another aspect, each row of photodetectors 18a-18d includes an equal number of photodetectors. In another aspect, photodetector array 18 includes an array in which each row of photocells and/or photoresistors 18a-18d includes two photocells and/or photoresistors 18a-18d. In another aspect, photodetector array 18 includes an even number of photodetectors 18a-18d.

In one aspect, as shown in FIGS. 2-6, photodetector array 18 includes an array in which photodetectors 18a-18d are arranged in two parallel rows. In another aspect, photodetector array 18 includes an array in which photodetectors 18a-18d are spaced apart from each other by gap 24. In another aspect, photodetector array 18 includes an array in which photodetectors 18a-18d are arranged in parallel relation so as to form a plurality of parallel columns and parallel rows of photodetectors 18a-18d. In another aspect, photodetector array 18 includes at least one or more rows of photodetectors 18a-18d having a different number of photodetectors 18a-18d. In another aspect, photodetector array 18 includes at least one of photodetectors 18a-18d spaced apart from one or more other adjacent photodetectors 18a-18d by gap 24. In another aspect, photodetector array 18 includes one or more photodetectors 18a-18d are in contiguous relation with one or more adjacent photodetectors 18a-18d.

In one aspect, photodetector array 18 is responsive to reception of light entering sensor 10 through aperture 20 to provide electrical an output representative of spatial location and/or orientation of an incident light with respect to the plane of photodetector array 18.

In one aspect of photodetector array 18, output signals (light intensity readings) of one or more photocells and/or photoresistors 18a-18d are detectably associable with relative positions of the one or more photocells and/or photoresistors 18a-18d within photodetector array 18. In another aspect of photodetector array 18, output signals (light intensity readings) of one or more photodetectors 18a-18d are detectably associable with relative orientations of one or more photodetectors 18a-18d within photodetector array 18. In yet another aspect of photodetector array 18, output signals (light intensity readings) of one or more photodetectors 18a-18d are detectably associable with relative positions of one or more photodetectors 18a-18d and spatial orientations of one or more photodetectors 18a-18d within photodetector array 18.

As shown in FIGS. 1 and 4, in one aspect, system 100 includes a processor 102 coupled to photodetector array 18. In one aspect, processor 102 serves to perform necessary calculations using the information received from photodetector array 18 to provide an output signal representative of azimuth and/or elevation angle of incident light relative to the plane of sensor 10. In one aspect, processor 102 is configured to detect light source on the basis of variation in light intensity readings detected at one or more regions of photodetector array 18 that are illuminated/activated by a light entering sensor 10 through aperture 20. In another aspect, signal processor 102 is configured to be responsive to output signals from photodetector array 18 and for evaluating output signals from photodetector array 18 and to calculate azimuth and/or elevation angle of incident light relative to the plane of sensor 10. In one aspect, output signals of photodetector array 18 comprise light intensity readings. In another aspect, processor 102 evaluates light intensity readings of photodetector array 18 and calculates azimuthal direction and/or elevation angle of incident light from the ratios of light intensity readings from photodetector array 18.

Figure 6:
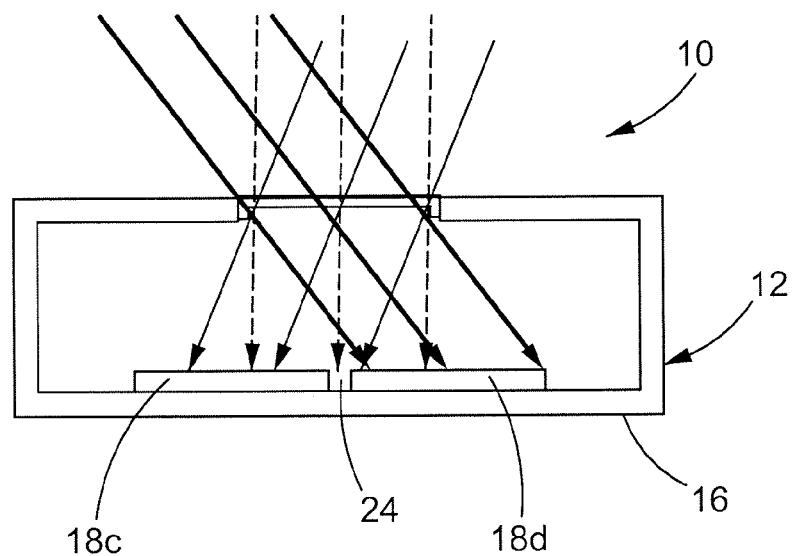
FIG. 6 is a schematic cross-sectional side view of the sensor of FIG. 1 showing light entering the sensor at different incident angles in accordance with an exemplary aspect of the present invention.
Figure 7:
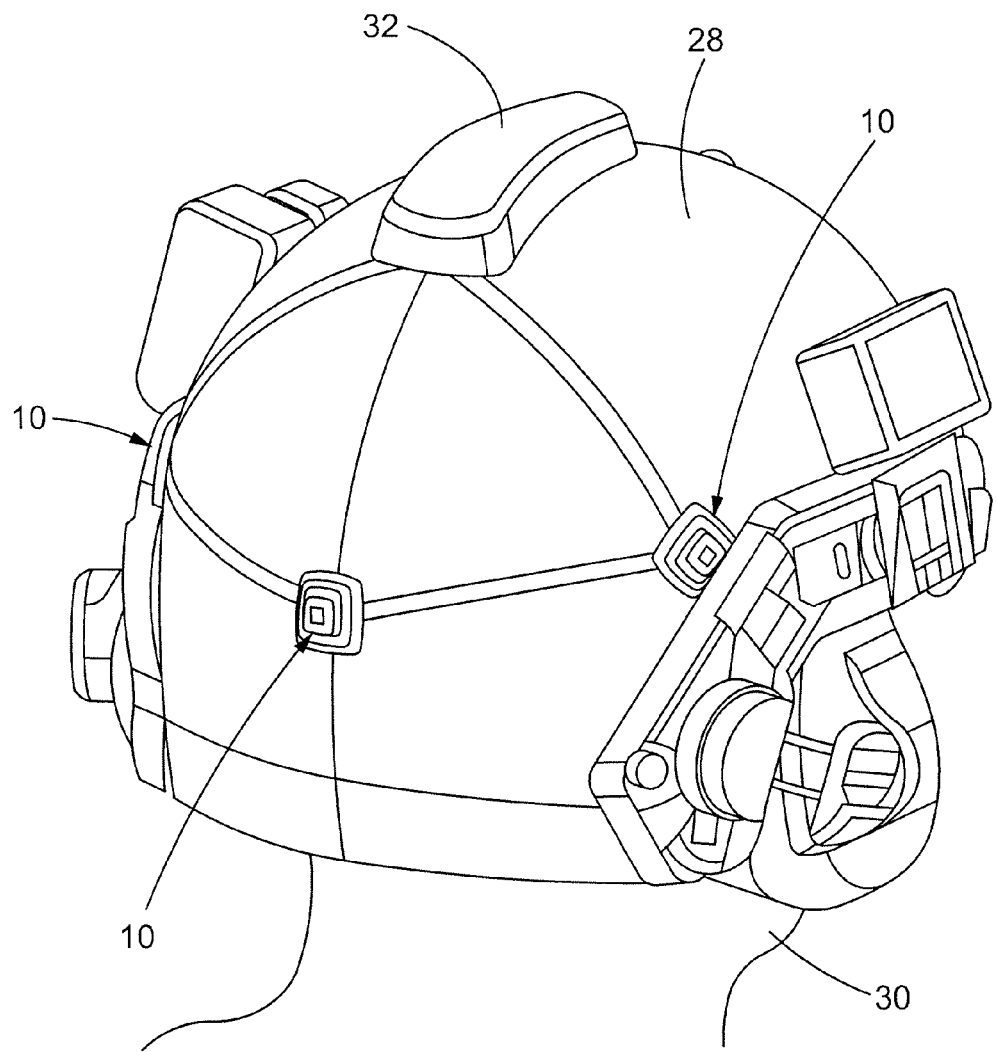
FIG. 7 shows the system of FIG. 1 having a plurality of sensors coupled to a helmet in accordance with an exemplary aspect of the present invention.

Referring to FIGS. 6 and 7, azimuth and elevation angle generally define an apparent position of an object in the sky, relative to a specific observation point (sensor 10 in the present instant). The observer 30 in FIG. 7, in this case wearing sensor 10, is typically (but need not be) located on the earth's surface. Azimuth typically is the compass bearing, relative to true (geographic) north, of a point on the horizon directly beneath an observed object (e.g., gunfire). Horizon is conventionally defined as an imaginary circle centered on observer 30 (or sensor 10), equidistant from the zenith (point straight overhead) and the nadir (point exactly opposite the zenith). Compass bearings are commonly measured clockwise in degrees from north. Azimuth angles can thus range from 0 degrees (north) through 90 (east), 180 (south), 270 (west), and up to 360 (north again).

In some aspects, an elevation angle, or an altitude, of an observed object (e.g., gunfire) as would be understood by one of ordinary skill in the art could be determined by finding the compass bearing on the horizon relative to true north (geographic north), and then measuring the angle between that point and the object, from the reference frame of the observer (the system for gunfire detection 10). Elevation angles for objects (e.g., gunfire) above the horizon can range from 0 (on the horizon) up to 90 degrees (at the zenith). Sometimes the range of the elevation coordinate is extended downward from the horizon to −90 degrees (the nadir). This can be useful when observer 30 (or sensor 10) is located at some distance above the surface of the earth, such as in an aircraft during a flight.

An azimuth direction and elevation angle of light source, such as gunfire, may be computed on the basis of light intensity readings of photocells 18 as follows:

As shown in FIG. 7, a plurality of sensors 10 may be mounted to a side of an infantry helmet 28, or any other headgear. For sensor 10 to be mountable to a side of infantry helmet 28 is particularly advantageous, because each soldier can have his/her own wearable sensors 10. Furthermore, when coupled to infantry helmet 28, sensor 10 can be used to identify the source of a single light source 360° in both azimuth and elevation relative to the helmet reference frame and display information that will draw the wearer to the origin of the light source. The helmet reference frame can be related to the earth reference frame through the use of a ground helmet tracker.

As illustrated in FIG. 7, in one aspect, sensors 10 may be coupled to helmet tracker 32 to expand the range of capabilities of helmet tracker 32 beyond just estimating and predicting the position and orientation of helmet 28. In another aspect, a plurality of sensors 10 may be coupled to helmet tracker 32 to broaden the range of view and help pinpoint direction or location of light source such as hostile fire. In an aspect, helmet tracker 32 comprises a processor and a Global Positioning System (GPS). In one aspect, two or more sensors 10 are positioned around different radial positions on helmet 28. In one aspect, sensor 10 and processor 102 and/or computer or database 104 is mounted to helmet 28. In another aspect, processor 102 and/or computer or database 104 are remotely located. In one aspect, examples of a helmet tracker 32 suitable for use in accordance with the present invention are described in U.S. Pat. Nos. 5,645,077 and 7,301,648, both of which are incorporated herein by reference in their entirety.

In one aspect, processor 102 and/or computer or database 104 includes one or more computers having one or more processors and memory (e.g., one or more nonvolatile storage devices). In some aspects, a memory or a computer readable storage medium of memory stores programs, modules and data structures, or a subset thereof for a processor to control and run the various systems and methods disclosed herein. In one aspect, a non-transitory computer readable storage medium having stored thereon computer-executable instructions which, when executed by a processor, perform one or more of the methods disclosed herein.

Figure 9:
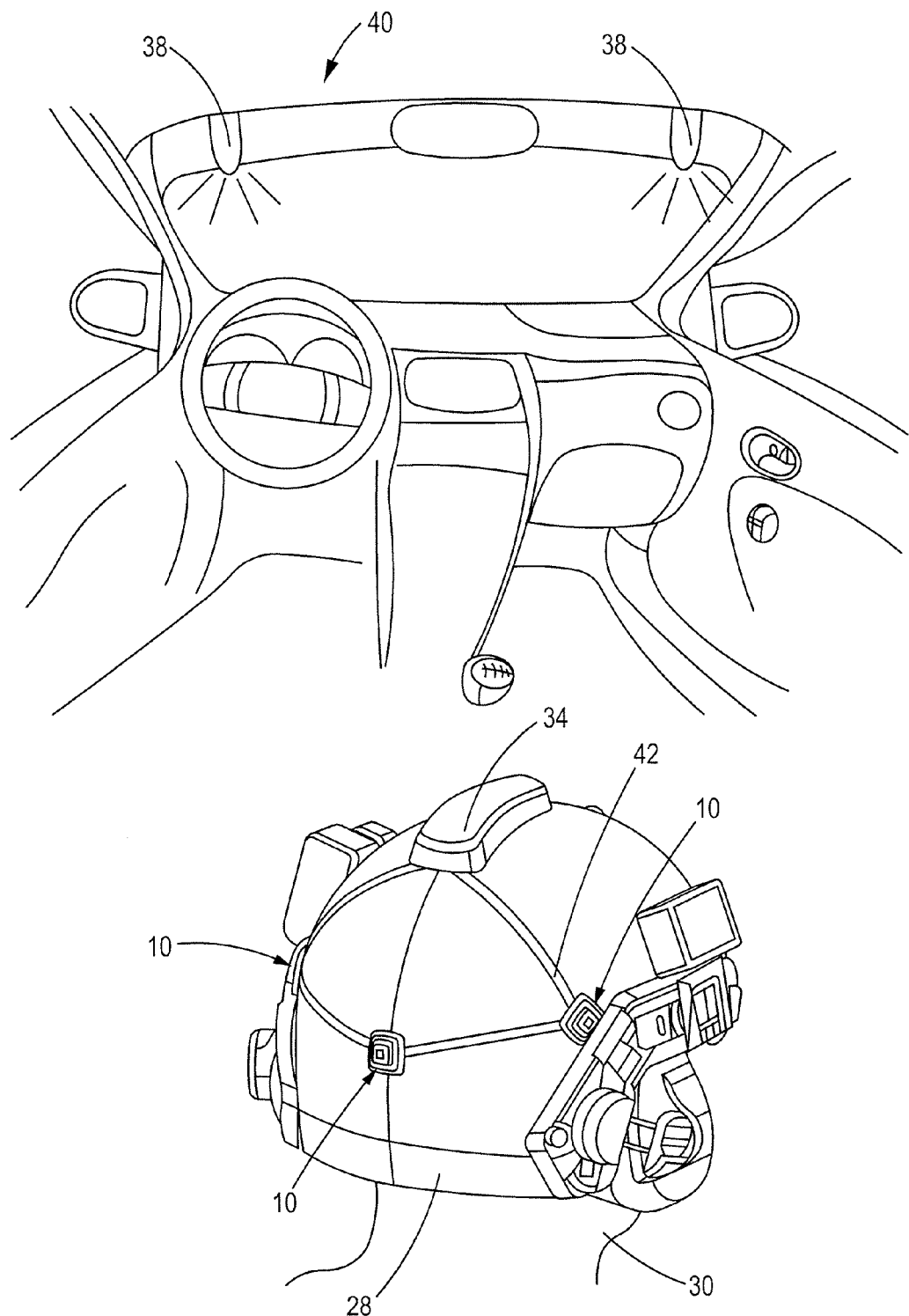
FIG. 9 shows the system of FIG. 1 having a plurality of sensors coupled to a helmet for helmet orientation detection in a vehicle in accordance with an exemplary aspect of the present invention.

Referring to FIG. 9, in one aspect, sensor 10 may be coupled to helmet 28 and used to detect the orientation of the helmet 28 relative to an object. In one aspect, the object is a vehicle. In one aspect, the object is a cockpit of an airplane. In one aspect, sensor 10 may be coupled to a housing 34 that houses a processor 102 (shown in FIG. 1) and a database 104 (shown in FIG. 1) via wiring 42. In one aspect, one or more light source 38 (such as light emitting diode) is mounted at a fixed and predetermined location in a canopy 40 of a vehicle or an aircraft (shown schematically).

In one aspect, light source 38 is a light emitting diode. In one aspect, light source 38 has a wave length in a range of from about 950 nm and about 1100 nm. In one aspect, light source 38 is light emitting diode configured to transmit a beam of light toward sensor 10. In one aspect, sensor 10 measures the beam of light and outputs an azimuth/elevation signal to processor 102. In one aspect, sensor 10 generates azimuth/elevation signal based on ratios of light intensity readings from photodetector array 18 comprising a plurality of photodetectors 18a-18d in sensor 10. In another aspect, each photodetector 18a-18d generates a voltage correlated to the intensity of light incident on its surface. In a further aspect, a processor converts each voltage into a digital number and then calculates light intensity ratios therefrom. In one aspect, a plurality of sensors 10 may be mounted to helmet 28 and configured to output a plurality of azimuth/elevation signals to processor 102. In one aspect, processor 102 receives the azimuth/elevation signal from the sensor 10 and calculates the orientation of the helmet 28 relative to the light emitting diode 38 based on the angle of incident light from light source 38 (e.g. light emitting diode) as measured by sensor 10.

In one aspect, processor 102 calculates the orientation of helmet 28 relative to the object to which light source 38 is mounted by first calculating the azimuth angle and elevation angle of light source 38 (such as a light emitting diode) based on the azimuth/elevation signal received from sensor 10. In one aspect, processor 102 then compares the measured azimuth angle and measured elevation angle to a predetermined azimuth angle and a predetermined elevation angle stored in database 104. In one aspect, the predetermined azimuth angle and elevation angle correspond to the location of light source 38 (such as a light emitting diode) when helmet 28 is pointing forward in canopy 40. Based on the difference between the measured azimuth and elevation angle compared to the stored azimuth angle and elevation angle, processor 102 calculates a new orientation of helmet 28 relative to light source 38 (such as a light emitting diode). In one aspect, examples of a motion tracking system and methods of using the same that are suitable for use in accordance with exemplary aspects of the present invention are described in U.S. Pat. Nos. 6,409,687 and 7,000,469 both of which are incorporated herein by reference in their entirety.

A system for detecting a light source in accordance with the present invention can be advantageously configured for use in a battle field or in any hostile fire situation. For a militaristic application, the system for detecting a light source may be advantageously used by an infantry soldier to detect the presence and/or whereabouts of a hostile fire, such as hostile gunfire, and use the knowledge of the bearing of the location of the detected hostile fire to counter the danger posed by the hostile fire. The light source that can be detected by the system for detecting a light source includes a muzzle flash. The system for detecting a light source is versatile because it can be dimensioned to be relatively small and wearable on a headgear or any suitable part of the body of a user, for example, a soldier. Moreover, the system for detecting a light source can be coupled to an infantry helmet and used to identify the source of a single light source 360° in both azimuth and elevation relative to the helmet reference frame. Importantly, the azimuth and elevation of the light source can be displayed in a usable format to alert the infantry helmet wearer to the origin of the light source. Furthermore, the helmet reference frame can be related to the earth reference frame through the use of a ground helmet tracker.

Figure 10:
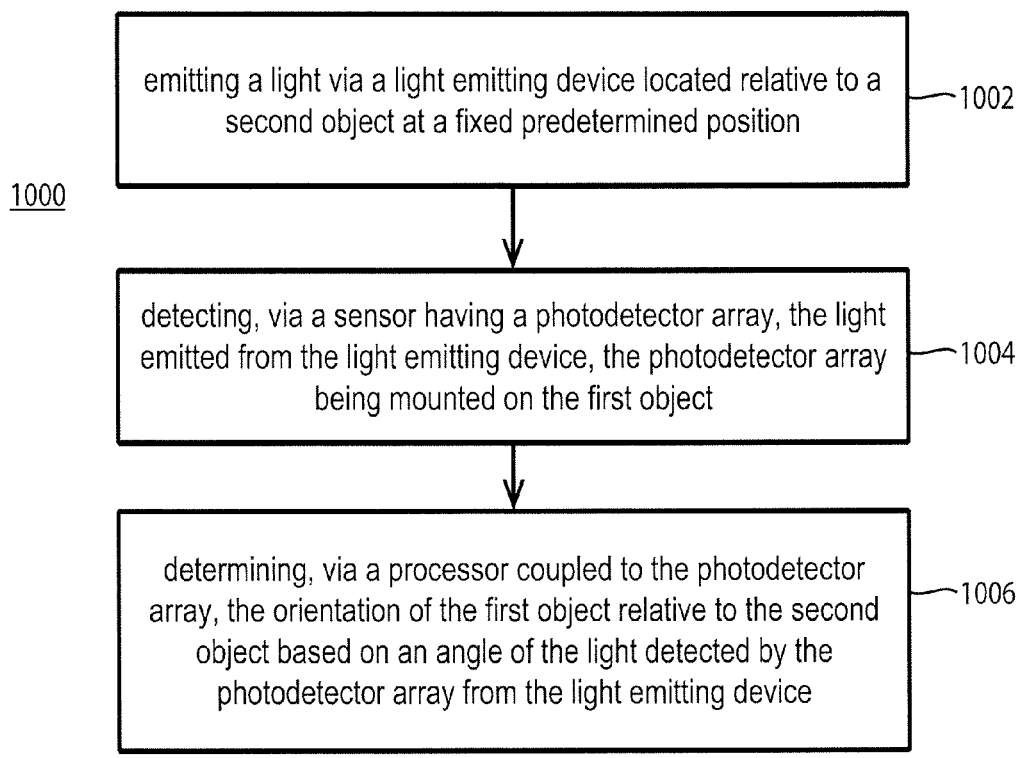
FIG. 10 depicts an example flow diagram of a method for tracking an orientation of a first object in accordance with aspects of the present invention.

FIG. 10 illustrates an example flow diagram of a method 1000 for tracking an orientation of a first object in accordance with aspects of the present invention. As shown in FIG. 10, in block 1002, emitting a light via a light emitting device located relative to a second object at a fixed predetermined position.

In block 1004, detecting, via a sensor having a photodetector array, the light emitted from the light emitting device, the photodetector array being mounted on the first object.

In block 1006, determining, via a processor coupled to the photodetector array, the orientation of the first object relative to the second object based on an angle of the light detected by the photodetector array from the light emitting device.

Figure 11:
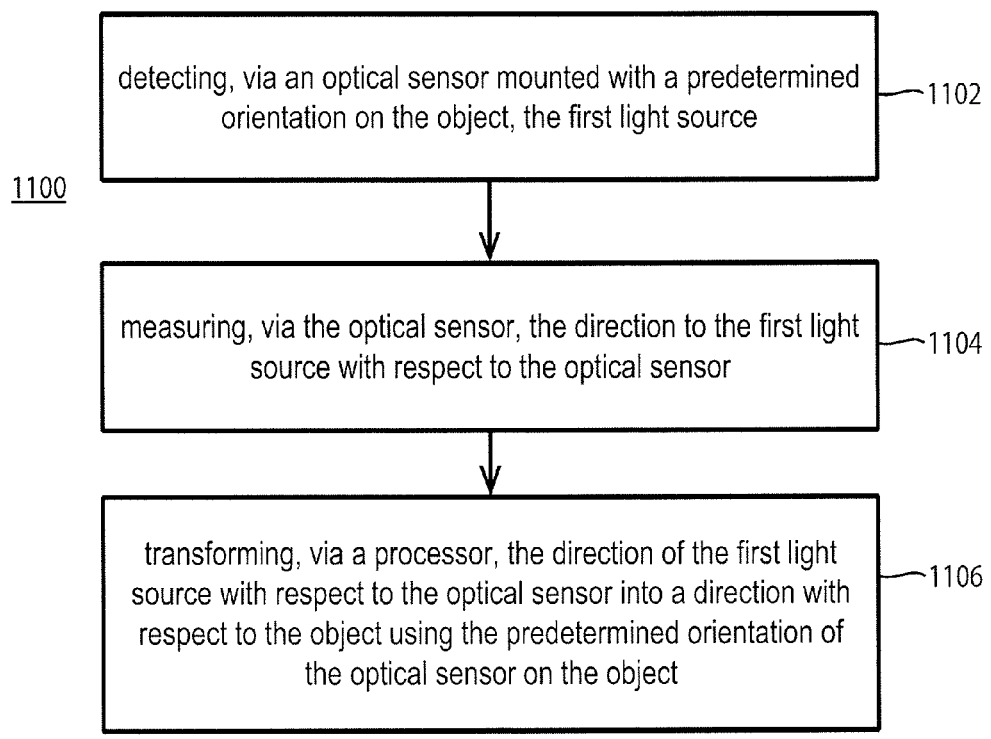
FIG. 11 depicts an example flow diagram of a method for detecting a direction from an object to a first light source in accordance with aspects of the present invention.

FIG. 11 illustrates an example flow diagram of a method 1100 for detecting a direction from an object to a first light source in accordance with aspects of the present invention. As shown in FIG. 11, in block 1102, detecting, via an optical sensor mounted with a predetermined orientation on the object, the first light source.

In block 1104, measuring, via the optical sensor, the direction to the first light source with respect to the optical sensor.

In block 1106, transforming, via a processor, the direction of the first light source with respect to the optical sensor into a direction with respect to the object using the predetermined orientation of the optical sensor on the object.

Figure 12:
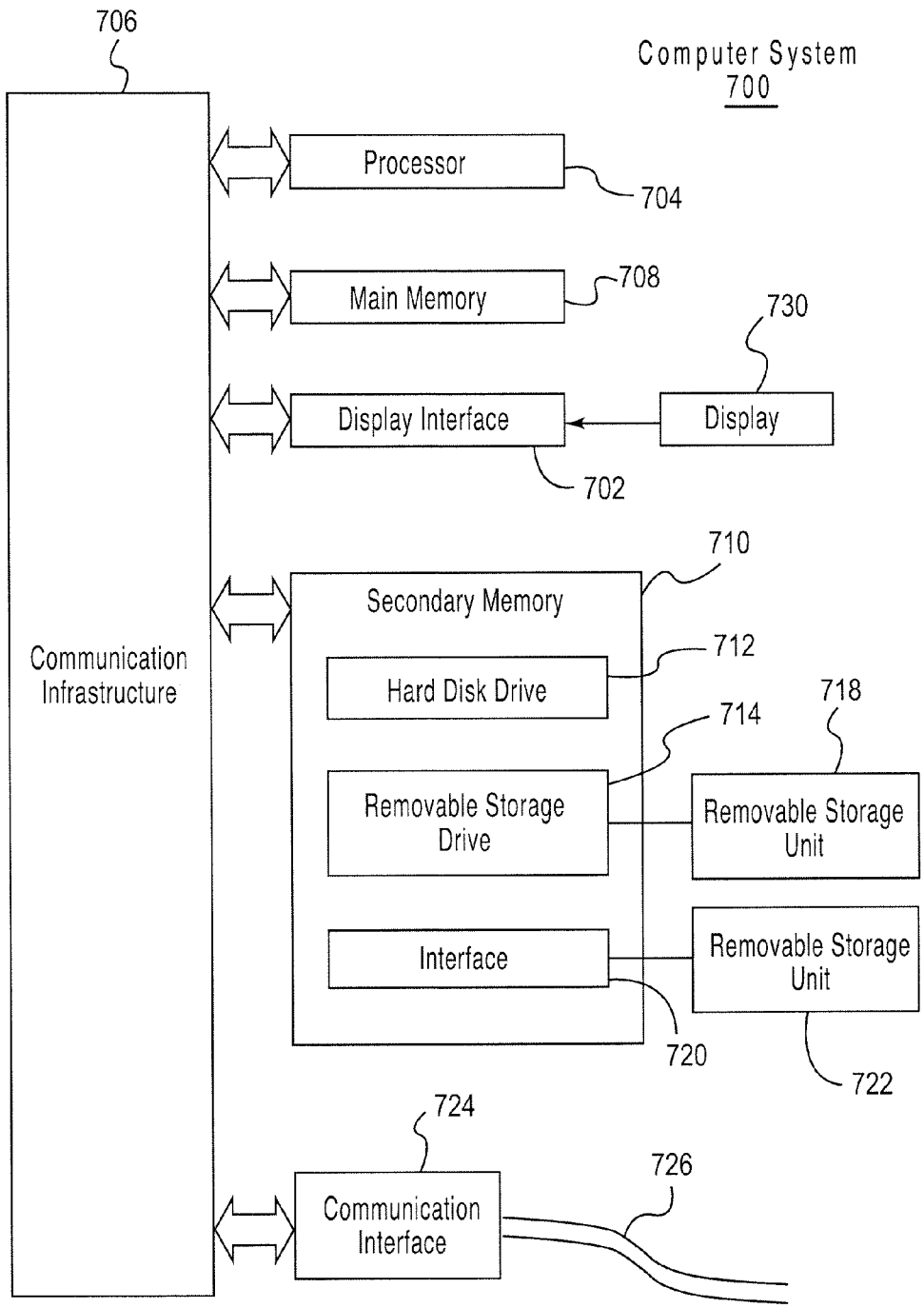
FIG. 12 depicts a computer system for implementing various aspects of the present invention.

Aspects of the present invention may be implemented using hardware, software, or a combination thereof and may be implemented in one or more computer systems or other processing systems. In one variation, aspects of the invention are directed toward one or more computer systems capable of carrying out the functionality described herein. An example of such a computer system 700 is shown in FIG. 12.

Computer system 700 includes one or more processors, such as processor 704. The processor 704 is connected to a communication infrastructure 706 (e.g., a communications bus, a cross-over bar, or a network). Various software aspects are described in terms of this exemplary computer system. After reading this description, it will become apparent to a person skilled in the relevant art(s) how to implement aspects of the invention using other computer systems and/or architectures.

Computer system 700 can include a display interface 702 that forwards graphics, text, and other data from the communication infrastructure 706 (or from a frame buffer not shown) for display on a display unit 730. Computer system 700 also includes a main memory 708, such as random-access memory (RAM), and may also include a secondary memory 710. The secondary memory 710 may include, for example, a hard disk drive 712 and/or a removable storage drive 714, representing a floppy disk drive, a magnetic tape drive, an optical disk drive, etc. The removable storage drive 714 reads from and/or writes to a removable storage unit 718 in a well-known manner. Removable storage unit 718 represents a floppy disk, a magnetic tape, a thumb drive, an optical disk, etc., which is read by and written to removable storage drive 714. As will be appreciated, the removable storage unit 718 includes a computer usable storage medium having stored therein computer software and/or data.

In alternative variations, secondary memory 710 may include other similar devices for allowing computer programs or other instructions to be loaded into computer system 700. Such devices may include, for example, a removable storage unit 722 and an interface 720. Examples of such may include a program cartridge and a cartridge interface (such as that found in video game devices), a removable memory chip (such as an erasable programmable read-only memory (EPROM) or a programmable read-only memory (PROM)) and associated socket, and other removable storage units 722 and interfaces 720, which allow software and data to be transferred from the removable storage unit 722 to computer system 700.

Computer system 700 may also include a communications interface 724. Communications interface 724 allows software and data to be transferred between computer system 700 and external devices. Examples of communications interface 724 may include a modem, a network interface (such as an Ethernet card), a communications port, a Personal Computer Memory Card International Association (PCMCIA) slot and card, etc. Software and data transferred via communications interface 724 are in the form of signals, which may be electronic, electromagnetic, optical, or other signals capable of being received by communications interface 724. These signals are provided to communications interface 724 via a communications path (e.g., channel) 726. This path 726 carries signals and may be implemented using wire or cable, fiber optics, a telephone line, a cellular link, a radio frequency (RF) link, and/or other communications channels. In this document, the terms "computer program medium," "computer-usable medium," and "computer-readable medium" are used to refer generally to media such as a removable storage drive 714, a hard disk installed in hard disk drive 712, and signals. These computer program products provide software to the computer system 700. Aspects of the invention are directed to such computer program products.

Computer programs (also referred to as computer control logics) are stored in main memory 708 and/or secondary memory 710. Computer programs may also be received via communications interface 724. Such computer programs, when executed, enable the computer system 700 to perform the features in accordance with aspects of the present invention, as discussed herein. In particular, the computer programs, when executed, enable the processor 704 to perform such features. Accordingly, such computer programs represent controllers of the computer system 700.

In a variation where aspects of the invention are implemented using software, the software may be stored in a computer program product and loaded into computer system 700 using removable storage drive 714, hard disk drive 712, or communications interface 720. The control logic (software), when executed by the processor 704, causes the processor 704 to perform the functions as described herein. In another variation, aspects of the invention are implemented primarily in hardware using, for example, hardware components, such as application-specific integrated circuits (ASIC's). Implementation of the hardware state machine so as to perform the functions described herein will be apparent to persons skilled in the relevant art(s).

In yet another variation, aspects of the invention are implemented using a combination of both hardware and software.

While aspects of the present invention have been described in connection with preferred implementations, it will be understood by those skilled in the art that variations and modifications described above may be made without departing from the scope hereof. Other aspects will be apparent to those skilled in the art from a consideration of the specification or from a practice of the aspects of the invention disclosed herein.

It will be appreciated by those skilled in the art that changes could be made to the exemplary aspects shown and described above without departing from the broad inventive concept thereof. It is understood, therefore, that this invention is not limited to the exemplary aspects shown and described, but it is intended to cover modifications within the spirit and scope of the present invention as defined by the claims. For example, specific features of the exemplary aspects may or may not be part of the claimed invention and features of the disclosed aspects may be combined.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed is:

1. A system for tracking an orientation of a first object, the system comprising:
    a light emitting device located relative to a second object at a fixed predetermined position;
    a sensor including a photodetector array configured to receive incident light emitted from the light emitting device, the photodetector array being mounted on the first object; and
    a processor coupled to the photodetector array, the processor being configured to determine the orientation of the first object relative to the second object based on an angle of incident light detected by the photodetector array from the light emitting device,
    wherein the sensor includes:
    a housing having a front side and a back side, the back side being opposed to the front side and spaced therefrom, the photodetector array being located at the back side wall within the housing and the housing being mounted to the first object; and
    an aperture extending through the front side of the housing and configured to expose the photodetector array to an incident light from the light emitting device.

2. The system of claim 1, wherein the processor is further configured to determine the orientation of the first object based on a variation in light intensity detected in one or more regions of a light-receiving surface of the photodetector array impinged by at least a portion of the incident light from a distant light source.

3. The system of claim 2, wherein the processor is further configured to arithmetically calculate at least one of: a measured azimuth direction and a measured elevation angle of the incident light from the light emitting device to determine a measured position of the light emitting device.

4. The system of claim 3, wherein the processor is further configured to arithmetically calculate at least one of: the measured azimuth direction and the measured elevation angle of the incident light from the light emitting device based on ratios of light intensity readings from the photo detector array.

5. The system of claim 3, wherein the processor is further configured to:
    store the predetermined position of the light emitting device in memory, the predetermined position of the light emitting device including a predetermined azimuth direction and a predetermined elevation angle,
    determine a difference between the at least one of: the measured azimuth direction and the measured elevation angle of the incident light from the light emitting device to at least one of: the initial azimuth direction and the initial elevation angle, and
    calculate the orientation of the first object based on the difference.

6. The system of claim 1, wherein the housing includes a plurality of housings, and wherein the plurality of housings is mounted to the first object.

7. The system of claim 1, wherein the light emitting device is mounted inside a vehicle or cockpit.

8. The system of claim 1, wherein the light emitting device comprises a light emitting diode.

9. The system of claim 1, wherein the object comprises a helmet.

10. The system of claim 1, wherein the light source comprises gunfire or a muzzle flash.

11. A system for detecting a direction from an object to a first light source, the system comprising:
    an optical sensor mounted with a predetermined orientation on the object, the optical sensor including a photodetector array and being configured to detect the first light source and to measure the direction to the first light source with respect to the optical sensor; and a processor configured to transform the direction of the first light source with respect to the optical sensor into a direction with respect to the object using the predetermined orientation of the optical sensor on the object;

wherein the optical sensor includes:
- a housing having a front side and a back side, the back side being opposed to the front side and spaced therefrom, the photodetector array being located at the back side wall within the housing and the housing being mounted to the object; and
- an aperture extending through the front side of the housing and configured to expose the photodetector array to an incident light from the light emitting device.

12. The system of claim 11, wherein the first light source comprises gunfire or a muzzle flash.

13. The system of claim 11, further comprising:
an inertial sensor mounted on the object for determining the orientation of the object with respect to an external reference frame; and
wherein the processor is further configured to transform the direction of the first light source with respect to the object into a direction with respect to the external reference frame.

14. The system of claim 13, further comprising:
a second light source at a predetermined location in an environment surrounding the object that at certain times enters a field of view of the optical sensor as a result of the motion of the object;
a determining module configured to determine at the times a direction from the optical sensor to the second light source; and
wherein the processor is further configured to update the orientation of the inertial sensor using the direction from the optical sensor to the second light source.

15. A method for tracking an orientation of a first object, the method comprising:
emitting light via a light emitting device located relative to a second object at a fixed predetermined position;
detecting, via a sensor including a photodetector array, the light emitted from the light emitting device, the photodetector array being mounted on the first object; and
determining, via a processor coupled to the photodetector array, the orientation of the first object relative to the second object based on an angle of the light detected by the photodetector array from the light emitting device,
wherein the sensor includes:
- a housing having a first side and a second side, the second side being opposite to the first side and spaced therefrom, the photodetector array being located proximal to the second side within the housing and the housing being mounted to the first object; and
- an aperture extending through the first side of the housing and configured to expose a plurality of photodetectors of the photodetector array to incident light from the first light source.

16. A method for detecting a direction from an object to a first light source, the method comprising:
detecting, via an optical sensor including a photodetector array mounted with a predetermined orientation on the object, the first light source;
measuring, via the optical sensor, the direction to the first light source with respect to the optical sensor; and
transforming, via a processor, the direction of the first light source with respect to the optical sensor into a direction with respect to the object using the predetermined orientation of the optical sensor on the object,
wherein the optical sensor includes:
- a housing having a first side and a second side, the second side being opposite to the first side and spaced therefrom, the photodetector array being disposed proximal to the second side within the housing and the housing being mounted to the object; and
- an aperture extending through the first side of the housing and configured to expose a plurality of photo detectors of the photodetector array to incident light from the first light source.

17. A system for tracking an orientation of a first object, the system comprising:
emitting means for emitting light, wherein the emitting means is located relative to a second object at a fixed predetermined position;
detecting means for detecting the light emitted from the emitting means, the detecting means being including a photodetector array and being mounted on the first object; and
determining means for determining the orientation of the first object relative to the second object based on an angle of the light detected by the detecting means,
wherein the detecting means for detecting the light includes:
- a housing including a first side and a second side, the second side being opposite to the first side and spaced therefrom, the photodetector array being disposed proximal to the second side within the housing and the housing being mounted to the first object; and
- an aperture extending through the first side of the housing and configured to expose a plurality of photo detectors of the photodetector array to incident light from the emitting means.

18. A system for detecting a direction from an object to a first light source, the system comprising:
detecting means for detecting first light, the detecting means being including a photodetector array and being mounted with a predetermined orientation on the object;
measuring means for measuring the direction to the first light source with respect to the detecting means; and
transforming means for transforming the direction of the first light source with respect to the detecting means into a direction with respect to the object using the predetermined orientation of the detecting means,
wherein the detecting means includes:
- a housing including a first side and a second side, the second side being opposite to the first side and spaced therefrom, the photodetector array being disposed proximal to the second side within the housing and the housing being mounted to the object, and
- an aperture extending through the first side of the housing, and configured to expose a plurality of photo detectors of the photodetector array to incident light from the first light source.

19. A non-transitory computer-readable medium having control logic stored therein for causing a processor of a computer to track an orientation of a first object, the control logic comprising:
code for emitting light via a light emitting device located relative to a second object at a fixed predetermined position;
code for detecting, via a sensor having a photodetector array, the light emitted from the light emitting device, the photodetector array being mounted on the first object; and code for determining, via a processor coupled to the photodetector array, the orientation of the first object relative to the second object based on an angle of the light detected by the photodetector array from the light emitting device, wherein the sensor includes:
- a housing having a first side and a second side, the second side being opposite to the first side and spaced therefrom, the photodetector array being disposed proximal to the second side within the housing and the housing being mounted to the first object, and
- an aperture extending through the first side of the housing and configured to expose a plurality of photo detectors of the photodetector array to incident light from the light emitting device.

20. A non-transitory computer-readable medium having control logic stored therein for causing a processor of a computer to detect a direction from an object to a first light source, the control logic comprising:

code for detecting, via an optical sensor including a photodetector array mounted with a predetermined orientation on the object, the first light source;

code for measuring, via the optical sensor, the direction to the first light source with respect to the optical sensor; and code for transforming, via a processor, the direction of the first light source with respect to the optical sensor into a direction with respect to the object using the predetermined orientation of the optical sensor on the object, wherein the optical sensor includes:
- a housing having a first side and a second side, the second side being opposite to the first side and spaced therefrom, the photodetector array being located proximal to the second side within the housing and the housing being mounted to the object, and
- an aperture extending through the first side of the housing and configured to expose a plurality of photo detectors of the photodetector array to incident light from the first light source.

* * * * *